United States Patent [19]
Scott

[11] Patent Number: 5,199,194
[45] Date of Patent: Apr. 6, 1993

[54] SEA BOTTOM SAMPLER

[75] Inventor: William J. Scott, St. John's, Canada

[73] Assignee: C-CORE-Centre for Cold Ocean Resources Eng., St. John's, Canada

[21] Appl. No.: 767,619

[22] Filed: Sep. 30, 1991

[51] Int. Cl.⁵ .............................. E02F 3/34; E02F 3/47
[52] U.S. Cl. ................................ 37/340; 294/68.23; 37/187; 37/307
[58] Field of Search ................ 37/71, 2 R, 54, 183 R, 37/186–188, DIG. 6, DIG. 8; 294/68.23

[56]    References Cited
U.S. PATENT DOCUMENTS

| | | | |
|---|---|---|---|
| 611,357 | 9/1898 | Dembinski | 37/71 |
| 2,136,890 | 11/1938 | Roberts | 294/68.23 |
| 2,621,428 | 12/1952 | Billings | 37/187 |
| 3,080,988 | 3/1963 | Redman | 294/68.13 |
| 3,641,689 | 2/1972 | Billings | 37/187 |
| 3,693,274 | 9/1972 | Piccagli | 37/71 |
| 3,762,078 | 10/1973 | Wetherbee | 37/54 |
| 4,129,329 | 12/1978 | Longo | 294/68.23 |
| 4,143,900 | 3/1979 | Longo | 37/187 |
| 4,908,966 | 3/1990 | Phillips et al. | 37/71 |

FOREIGN PATENT DOCUMENTS 234609  5/1960  Australia .......................... 294/68.23

OTHER PUBLICATIONS

Catalog of Geneq, Inc., Montreal, Quebec H1H 1H5 Canada (undated loose-leaf) May 1990, selected pages. "Technical Information on Alluvial Mining Company, Ltd." published by Alluvial Mining Company Ltd.

Primary Examiner—Randolph A. Reese
Assistant Examiner—Spencer Warnick
Attorney, Agent, or Firm—Jones, Tullar & Cooper

[57]    ABSTRACT

The invention relates to an apparatus, suitable for deployment from small vessels, for obtaining samples of materials from the sea bottom and, more specifically, to a multi-bucket sampler particularly suited for, but not restricted to, gathering samples from bottoms comprising hard or compacted materials and/or having coarse matter, such as gravel, distributed therein. In one embodiment the sampler comprises, in general, a dual bucket assembly pivotally attached to a frame, cover means for the buckets, and an actuator for pivoting the buckets from an open position wherein the buckets can penetrate the bottom to a closed position wherein the buckets are urged against the cover. The apparatus is designed to achieve maximum penetration of the seabed and to prevent washout of the materials collected upon recovery. The dual buckets provide sample duplication which may be used to assess local variability of bottom conditions.

21 Claims, 6 Drawing Sheets

SEA BOTTOM SAMPLER

FIELD OF THE INVENTION

The invention relates to an apparatus for collecting samples of materials from the sea bottom.

BACKGROUND

Devices for collecting samples of seabed materials, in particular those which are suitable for deployment from a small fishing vessel, for example a fishing boat 10 to 12 meters in length, typically comprise an open cavity which is closable by one or two curved jaws, or have instead, two or more curved clamshell buckets which close together. Closure is generally effected by a spring mechanism which is cocked on the surface and which is released upon contact with the bottom, by fall of a weight released by contact with the bottom, or by an upward pull on the cable which recovers the sampler. However, tools of these types are generally unsuccessful in collecting samples from hard or compacted bottoms because they fail to penetrate on impact. The limitation of penetration arises in part from the curvilinear configuration of the jaws at their ends, and in part because the sampler is light in weight. In addition, when multi-jaw type devices close on samples from bottoms comprising gravel or coarser material, the jaws are frequently prevented from complete closure by cobbles or boulders which catch in the opening, thus allowing finer material to be washed out during recovery of the tool. When the closure is effected by an upward pull on the recovery cable, the sampler is unweighted at the moment when greatest weight is required to maintain penetration during closure. Furthermore, such devices yield only a single sample. To assess the variability of the bottom, several casts must be made, necessitating anchorage of the vessel. If the vessel is not anchored, the casts may represent different areas of the bottom as the vessel drifts between the casts.

SUMMARY OF THE INVENTION

The present invention overcomes the aforementioned disadvantages by providing a sampler in which maximum penetration of the buckets into the seabed can occur upon impact with the bottom, and which prevents washout of materials contained within the buckets during recovery of the sampler. In general, the present apparatus is provided with a multi-bucket assembly in which each bucket is pivotally connected to a frame. The buckets are designed such that the surfaces thereof which penetrate the bottom are vertical upon impact. Since vertical surfaces encounter least resistance from bottom materials, penetration may be achieved even into hard on compacted bottoms. Some or all of the penetrating or leading edges may be fitted with teeth in order to improve penetration into coarse materials.

The buckets are arranged to close upwardly and preferably against a cover or shield, instead of inwardly against each other, so that cobbles and boulders tend to fall away from the closing edges, thus reducing the possibility of incomplete closure and loss of finer materials upon recovery of the sampler. Even in the instance where an object prevents a bucket or buckets from completely closing against the cover, the generally horizontal attitude of the buckets upon recovery limits loss of the sample due to washout. In order to reduce water resistance against the sampler during transit to the bottom, the cover may be provided with means by which it opens or pivots when the buckets are in their open or descending position.

Because a plurality of independent buckets are utilized, the sampler of the present invention can provide multiple samples from a single cast, thereby enabling at least some estimate of bottom variability. Anchoring of the vessel is thus not required and, therefore, use of this invention represents a potential increase in the number of seabed sites from which multiple samples can be collected in a given period of time.

Further features and advantages of the present invention will become more apparent with reference to the description of the preferred embodiment detailed hereinbelow when taken in conjunction with the appended drawings.

DETAILED DESCRIPTION OF THE PREFERRED EMBODIMENT

Figure 1:
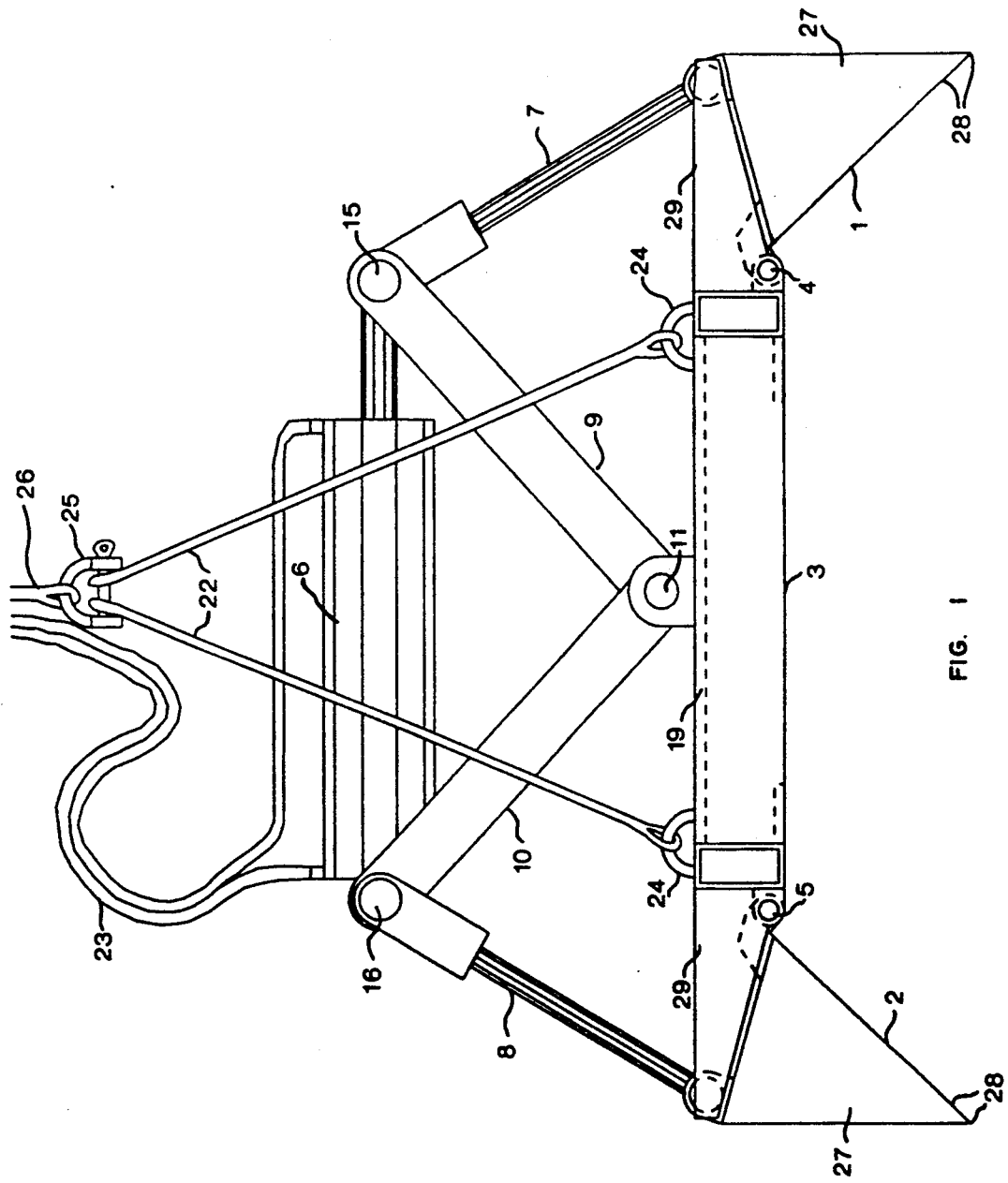
FIG. 1 is an elevation of the preferred embodiment of the invention, partly in section, with the buckets in their open or descending position.
Figure 2:
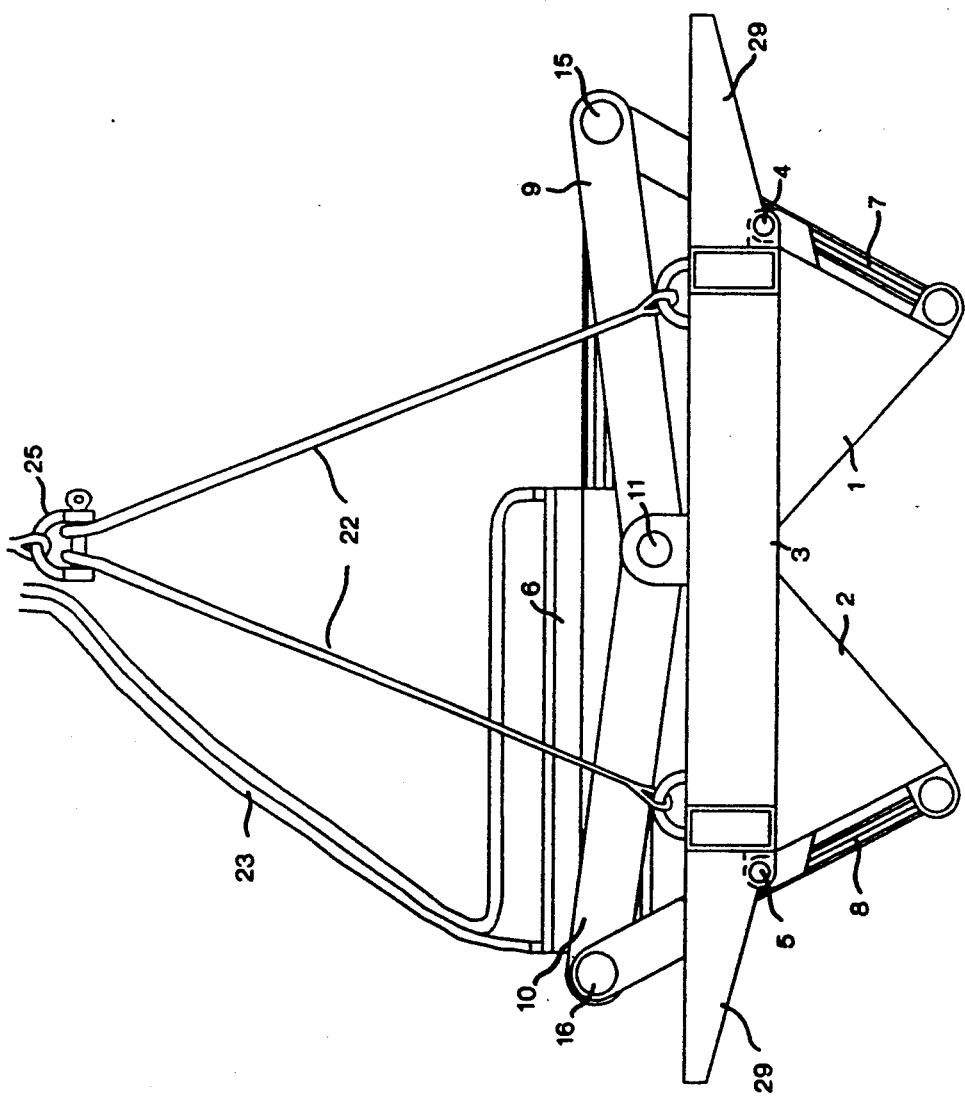
FIG. 2 is an elevation similar to that of FIG. 1 but with the buckets in their closed or ascending position.
Figure 3:
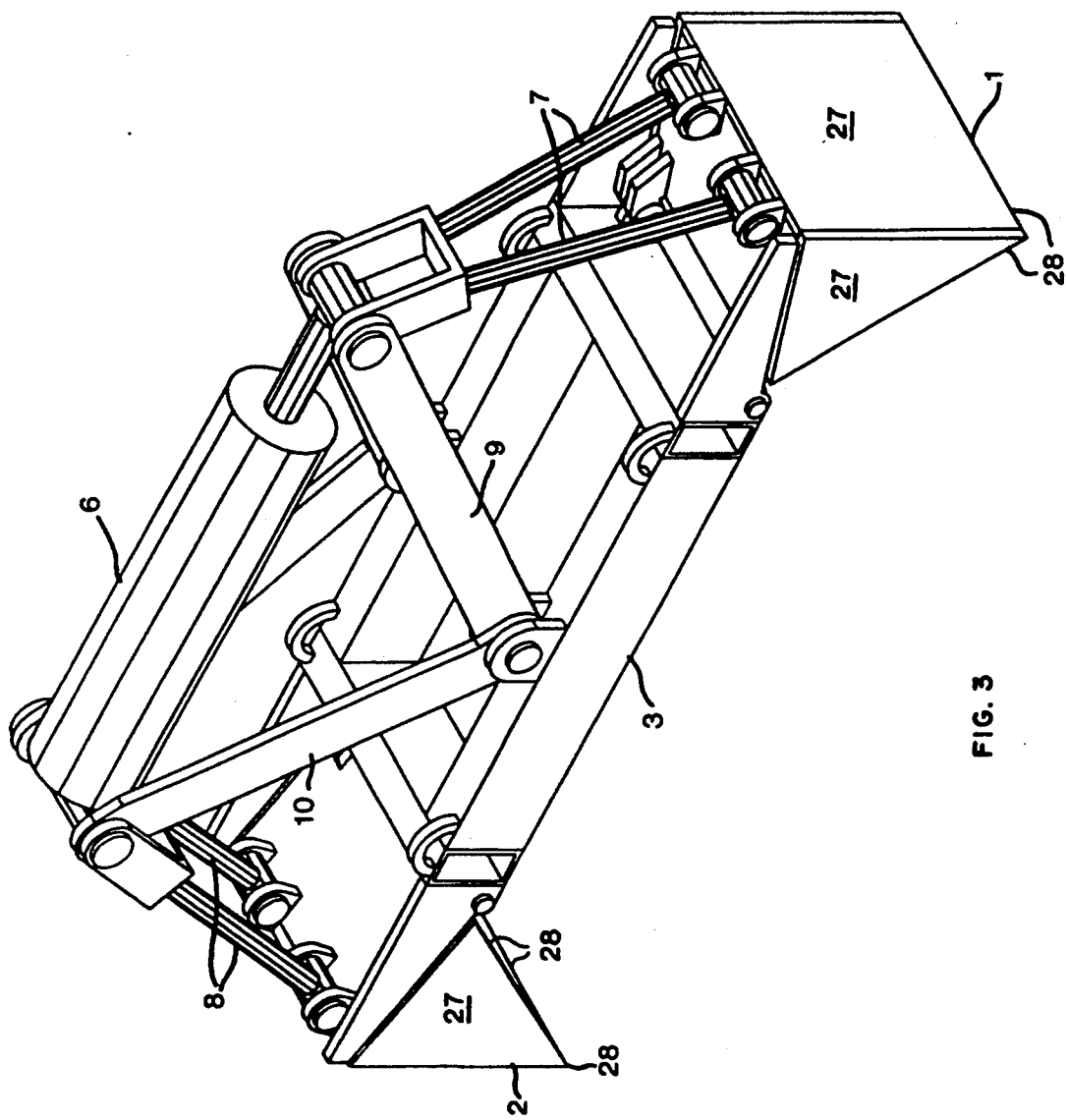
FIGS. 3 and 4 are perspective views of the apparatus shown in FIGS. 1 and 2, with some components omitted for clarity.
Figure 4:
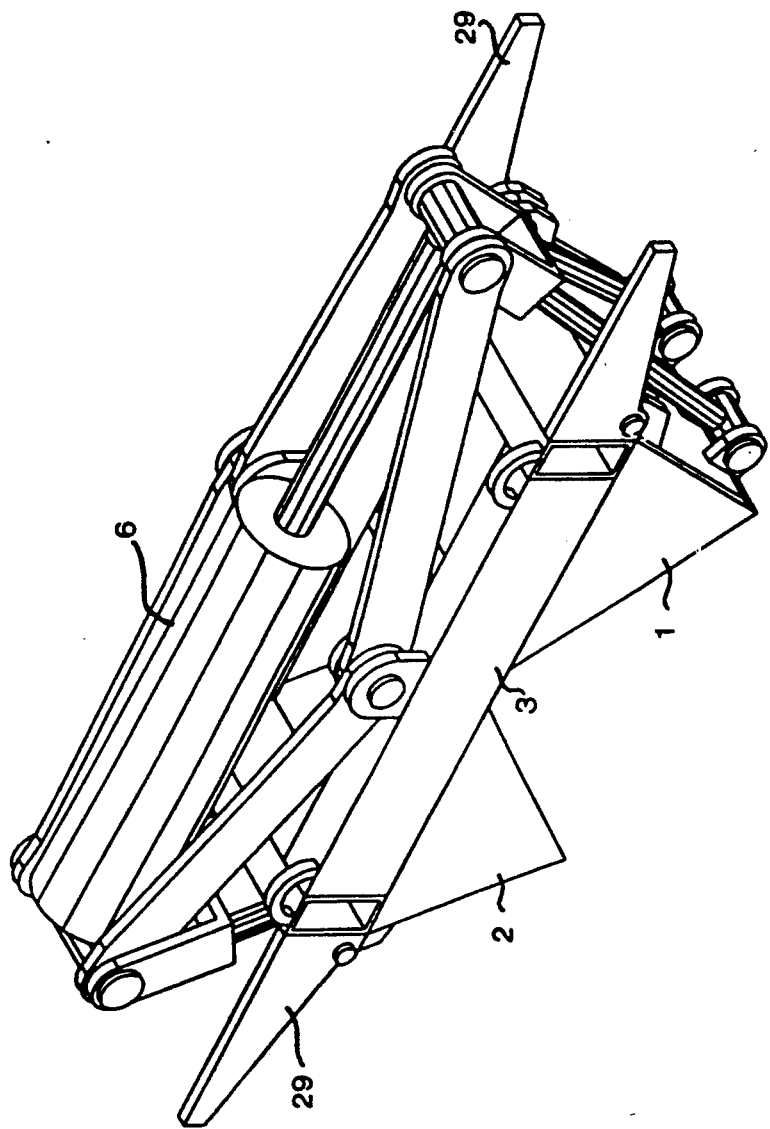
Figure 5:
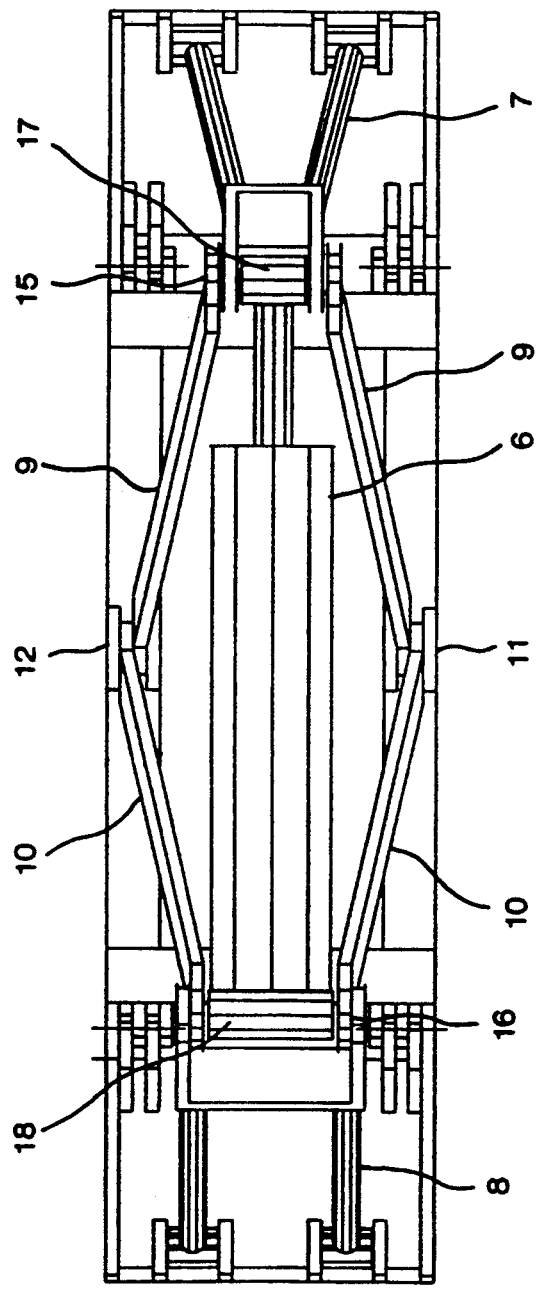
FIG. 5 is a plan view of the apparatus shown in FIG. 1.
Figure 6:
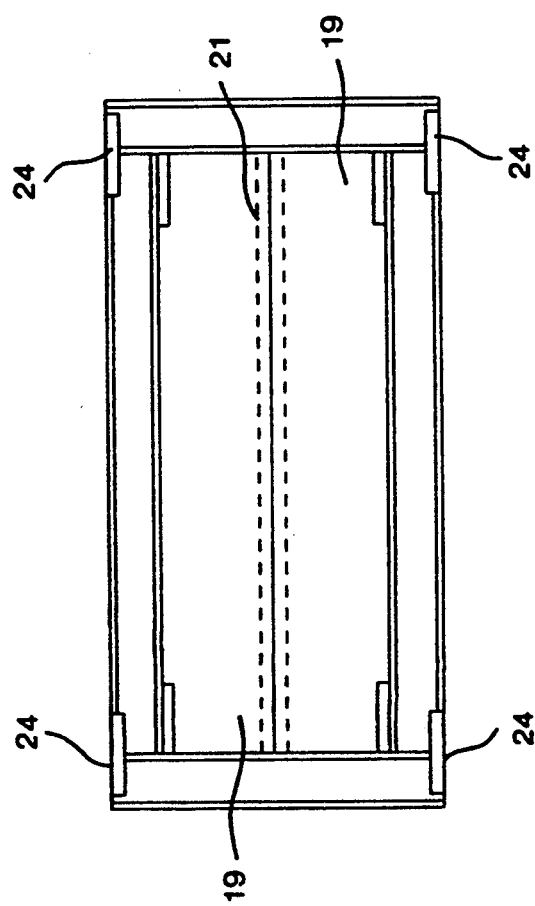
FIG. 6 is a plan view of the frame of the preferred embodiment.

FIGS. 1 to 6 illustrate an embodiment of the invention in which two buckets 1,2 are pivotally connected to a supporting frame 3 by hinges 4,5, respectively. Actuation means are provided to pivot the buckets 1,2 from an open position (see FIGS. 1 and 3), wherein the buckets 1,2 can penetrate the sea bottom, to a closed position (see FIGS. 2 and 4), wherein the buckets 1,2 can hold separate samples of the seabed materials for subsequent retrieval. In the preferred embodiment, the actuation means is comprised of a hydraulic cylinder 6 provided with suitable linkage means 7,8,9,10 to effect the required motion and/or to transmit the required forces for actuation. Linkages 9,10 are pivotally connected at one end thereof via pins 15,16 to the ends 17,18 of the hydraulic cylinder 6 and at their opposite end to the frame 3 by way of common pivot points 11,12. Connecting rods 7,8 are pivotally connected at one end thereof to the buckets 1,2, respectively, and at their opposite end to the ends 17,18, respectively, of the hydraulic cylinder 6. When the hydraulic cylinder is pressurized it extends, causing the buckets 1,2 to pivot inwardly about respective axes 4,5 from their open or descending position to their closed or ascending position wherein they assume a generally horizontal attitude as shown in FIG. 2.

Preferably, the frame 3 is provided with cover means for the buckets 1,2 against which the buckets 1,2 may be closed in order to contain the sample and to prevent washout during recovery. In the preferred embodiment, two cover plates 19 are hingedly connected to the frame 3. The plates 19 are pivotable between a substantially vertical position when the buckets 1,2 are in their open or descent position to a closed position wherein the plates 19 are held against a central supporting member 21 when the buckets 1,2 are in their closed or ascent position. The actuation of the cover means may be effected by the water resistance acting thereagainst when descending or ascending or may alternately be provided by separate mechanical means which is triggered by the closing of the buckets, by impact with the sea bottom, etc. While a solid cover plate rigidly attached to the frame may be utilized, it will be recognized that by employing a cover means which is operable upon descent, the water resistance encountered by the sampler will be greatly reduced. This leads to a greater drop velocity for the sampler and, therefore, greater kinetic energy upon impact with the bottom. With greater kinetic energy comes the potential for greater penetration for a given mass of sampler or, if penetration depth is already sufficient, the possibility of a reduction in the weight of the sampler making such a sampler more suited for deployment from a small vessel.

In order to obtain maximum penetration of the buckets upon impact, the surfaces of the buckets which penetrate the bottom are rectilinear in the vertical direction, at least to the designed depth of penetration, when the buckets are in their penetration, i.e. open, position; in the horizontal direction, these surfaces may be rectilinear or curvilinear. In the preferred embodiment shown in FIGS. 1 and 3 having the buckets 1,2 in their open position, the penetration surfaces 27 are planar, i.e. rectilinear in both the vertical and horizontal directions. The penetrating or leading edges 28 of the surfaces 27 preferably lie in the same plane or are configured to conform to the shape of the cover or shield against which they are closed. The penetrating edges 28 may also be provided with teeth (not shown) or be themselves serrated in order to improve penetration into coarse materials. In order to ensure verticality of the penetrating surfaces 27 of the buckets 1,2 during penetration, suitable stops 29 may be provided on frame 3 which limit the extent to which the buckets can pivot outwardly. Stops 29 also serve to reduce shock loading on the hydraulic cylinder 6 when the sampler impacts the sea bottom.

Once penetration has been achieved, the hydraulic cylinder 6 is actuated to close the buckets 1,2. The force required to close the buckets is greatest at the onset, but once the seabed material has failed, continuing closure requires less force. Preferably, the linkage means is designed to provide maximum force at the beginning of the stroke, and somewhat less near the end of the stroke when less is required. A geometrical analysis of the linkage reveals that as the angle between the axis of hydraulic cylinder 6 and the axis of connecting rod 8 (or connector rod 7) varies, the force applied by the cylinder 6 will vary. This force is proportional to the cosine of the angle so if the force applied by cylinder 6 is constant, the force exerted by each connecting rod to close its corresponding bucket will decrease as the angle increases. Accordingly, the force exerted by the connecting rod 8 (or 7) is maximum at the beginning of closure, for a constant cylinder force. Similarly, the force applied to the lip 28 of the bucket 2 is proportional to the sine of the angle between the axis of the connecting rod 8 and a line extending between the connection point of the rod with the bucket and the pivot point 5 of the bucket. As this angle decreases with closure of the bucket, the force applied to the bucket lips decreases. As a result, maximum force is applied to the bucket lips when the bucket is open. In the unlikely event that one bucket is prevented from completely closing, the other bucket can still close due to the floating nature of the hydraulic cylinder 6. In this regard, it is not necessary for the buckets to close simultaneously as it will be appreciated that the reaction force for closure of one bucket is provided by the opposite bucket.

The apparatus is preferably suspended from a cable 26 by means of a suitable set of frame support links 22 which are connected to eyes 24 on the frame 3 and to a shackle 25 which links them to the cable 26. Hydraulic hoses 23 for actuating the hydraulic cylinder 6 are led beside the cable 26 to the surface. It is contemplated that a special cable could be alternately provided which combines the functions of conducting hydraulic fluid up and down and support of the sampler.

While there has been shown and described a preferred embodiment of the present invention, it is intended to be illustrative rather than restrictive and it will be apparent that various modifications and alterations may be made thereto without departing from the spirit and scope of the appended claims. It will be appreciated that other bucket arrangements may be provided to meet specific needs. For example, where samples are required from seabeds having steeply sloping floors, a more stable four-bucket arrangement may be provided. A multi-bucket assembly may be of the type wherein the buckets are arranged to close radially inwardly or of the type comprising several dual-bucket samplers arranged in an array. In the case of the latter, a more comprehensive indication of bottom variability would be obtainable. These and other variations are encompassed within the following claims.

What is claimed is:

1. An apparatus for collecting samples of seabed materials comprising:
   a generally horizontal frame;
   cover means comprising at least one cover element pivotally connected to said frame for movement between a generally vertical open position when the apparatus is descending to a generally horizontal closed position when the apparatus is ascending;
   a plurality of buckets, said buckets each being below said cover and pivotally connected to said frame; and
   actuation means for pivoting each of said buckets from a downwardly open seabed penetrating position upwardly toward said cover means to a closed sample retaining position, said buckets each having a separate sample retaining position whereby each bucket is capable of independently retaining a sample when in said closed position.

2. The apparatus as claimed in claim 1, wherein said buckets have penetrating surfaces which are linear in the vertical direction, at least to the designed depth of penetration, when said buckets are in said seabed penetrating position.

3. The apparatus as claimed in claim 2, wherein said penetrating surfaces are planar.

4. The apparatus as claimed in claim 1, wherein said actuation means comprises a hydraulic cylinder and linkage means connecting said hydraulic cylinder to said buckets.

5. The apparatus as claimed in claim 4, wherein said linkage means includes a connecting rod connected to provide maximum force at the start of pivoting of said buckets from said open position.

6. The apparatus as claimed in claim 4, wherein the number of said buckets is two and wherein said frame is generally rectangular, said buckets being pivotally connected to said frame at opposite ends thereof for inward pivotal movement with respect thereto; and wherein said hydraulic cylinder is disposed generally parallel to said frame and generally transverse to the pivot axes of said buckets.

7. The apparatus as claimed in claim 1, wherein said cover means comprises a pair of plates pivotally attached to said frame, said plates being pivotable between an open position when the apparatus is descending to a closed position when the apparatus is ascending.

8. The apparatus as claimed in claim 6, wherein the frame is provided with stops extending outwardly from the ends of said frame to which said buckets are attached to limit the extent to which said buckets can pivot outwardly.

9. An apparatus for the recovery of samples from the sea bottom comprising:
   a generally horizontal frame;
   a plurality of buckets, said buckets each being pivotally connected to said frame, each of said buckets having an interior cavity at least partially enclosed by penetrating surfaces provided with leading edges thereon, said leading edges of the penetrating surfaces of each bucket being disposed generally in the same plane; and
   actuation means for pivoting each of said buckets from a seabed penetrating position wherein said plane is non-horizontal to a separated, generally horizontal, sample recovery position, wherein the plane of said leading edges of each of said buckets attains a generally horizontal attitude whereby a sample gathered into the cavity of each bucket is substantially prevented from being washed out upon recovery.

10. The apparatus as claimed in claim 9, wherein said penetrating surfaces are linear in the vertical direction, at least to the designed depth of penetration, when said buckets are in said seabed penetrating position.

11. The apparatus as claimed in claim 10, wherein said penetrating surfaces are planar.

12. The apparatus as claimed in claim 9, wherein said actuation means comprises a hydraulic cylinder and linkage means connecting said hydraulic cylinder to said buckets.

13. The apparatus as claimed in claim 12, wherein said linkage means includes a connecting rod connected to provide maximum force at the start of pivoting of said buckets from said open position.

14. The apparatus as claimed in claim 12, wherein the number of said buckets is two and wherein said frame is generally rectangular, said buckets being pivotally connected to said frame at opposite ends thereof for inward pivotal movement with respect thereto; and
   wherein said hydraulic cylinder is disposed generally parallel to said frame and generally perpendicular to the pivot axes of said buckets.

15. The apparatus of claim 9, wherein said frame includes a generally horizontal cover plate attached thereto.

16. The apparatus of claim 9, wherein said frame includes a generally horizontal cover plate pivotally attached thereto.

17. The apparatus of claim 9, wherein said buckets are spaced apart sufficiently to prevent contact therebetween when in said sample recovery position.

18. An apparatus for collecting samples of seabed materials comprising:
   generally rectangular frame means incorporating a cover;
   a pair of buckets pivotally connected to opposite ends of said frame, said buckets each being separately capable of retaining a sample; and
   actuation means for pivoting each of said buckets from a seabed penetrating position inwardly and upwardly toward said frame means to a generally horizontal sample retaining position against said frame means, each said bucket engaging only said frame means in said sample retaining position.

19. An apparatus for collecting samples of seabed materials, comprising:
   generally horizontal frame means;
   means for lowering said frame means toward a seabed and for raising said frame from said seabed;
   cover means pivotally connected to said frame for motion between an open position when said frame means is lowered and a generally horizontal closed position when said frame means is raised;
   at least one sample bucket pivotally mounted on said frame and having a penetrating surface with a leading edge, said at least one bucket each being pivotable between a first, seabed penetrating position and a second, independent sample collection position; and
   actuator means for pivoting said bucket to said first position to enable said leading edge and said penetrating surface to engage a seabed upon lowering of said frame and for pivoting said bucket to said second position to collect a seabed sample, said actuator means including linkage means to urge said leading edge toward said cover means to enable said bucket to retain a collected sample when in said second, sample collection position and when said frame is raised.

20. The apparatus of claim 19, wherein said at least one sample bucket includes first and second buckets mounted on said frame for pivotal motion toward and away from each other but spaced apart sufficiently to prevent said buckets from contacting each other when in said sample collection position, said actuator means being connected to both said buckets.

21. The apparatus of claim 20, wherein said penetrating surface of each said bucket is substantially vertical in said penetrating position, said buckets being pivoted toward each other and toward said cover means from said penetrating position to said sample collection position.

* * * * *